United States Patent [19]

Aime

[11] Patent Number: 5,431,040

[45] Date of Patent: Jul. 11, 1995

[54] METHOD FOR MEASURING THE HUMIDITY OF HOT AIR, APPARATUS FOR EMPLOYING THIS METHOD, AND A HOT AIR DRYING INSTALLATION INCLUDING THIS APPARATUS

[75] Inventor: Bruno Aime, Les Roches Premarie, France

[73] Assignee: Societe D'Automatisme de Production, Cognac, France

[21] Appl. No.: 237,470

[22] Filed: May 3, 1994

[30] Foreign Application Priority Data

May 21, 1993 [FR] France ................... 93 06113

[51] Int. Cl.6 .............................................. F26B 21/08
[52] U.S. Cl. ................................. 73/29.01; 73/29.02; 73/335.02
[58] Field of Search ................ 73/29.01, 29.02, 335.02

[56] References Cited

U.S. PATENT DOCUMENTS

| | | | |
|---|---|---|---|
| 4,221,058 | 9/1980 | Zagorzycki | 73/29.01 |
| 4,734,554 | 3/1988 | Tateda et al. | 73/335.02 |
| 4,872,340 | 10/1989 | de Yong | 73/335.02 |
| 4,893,508 | 1/1990 | Friedman | 73/335.02 |

FOREIGN PATENT DOCUMENTS

| | | |
|---|---|---|
| 2205197 | 5/1974 | France . |
| 1648303 | 3/1971 | Germany . |
| 2112662 | 9/1972 | Germany . |
| 3224761 | 1/1984 | Germany . |
| WO91/09292 | 6/1991 | WIPO . |
| WO92/21080 | 11/1992 | WIPO . |

OTHER PUBLICATIONS

Patent Abstracts of Japan–vol. 10, No. 223 (P–483) and JP-A-61 059 2525 Aug. 1986 2 Mar. 1986.

*Primary Examiner*—Richard E. Chilcot, Jr.
*Assistant Examiner*—Eric S. McCall
*Attorney, Agent, or Firm*—Kenyon & Kenyon

[57] ABSTRACT

The invention proposes that, under known conditions, hot air, for example that which circulates in a drying oven (1), shall be diluted with cool air of known humidity, for example air from outside, in order to obtain an air mixture the characteristics of which are suitable for conventional humidity sensors, for example a psychrometer; and that the humidity of the hot air shall be deduced from the known dilution conditions, the known humidity of the cool air, and the measured humidity of the air mixture.

For the dilution of the hot air, use is preferably made of a mixer (14) having an enclosure (15) connected to a suction source (16).

18 Claims, 3 Drawing Sheets

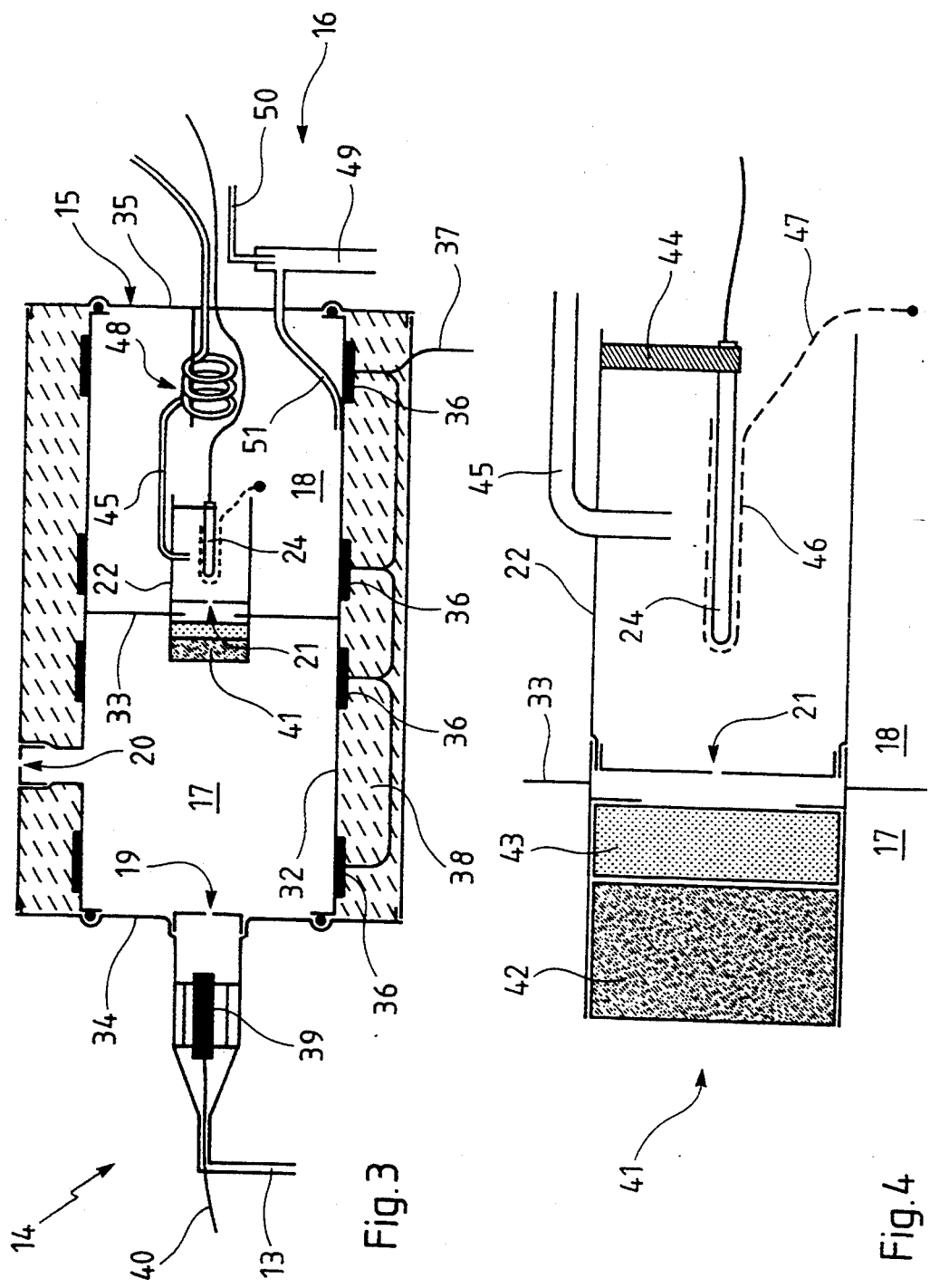

METHOD FOR MEASURING THE HUMIDITY OF HOT AIR, APPARATUS FOR EMPLOYING THIS METHOD, AND A HOT AIR DRYING INSTALLATION INCLUDING THIS APPARATUS

In its most general aspect, the invention relates to the measurement of humidity in air, and in a more particular aspect it relates to hot air drying installations.

It is already known to provide, for the purpose of carrying out such measurement with high precision, various methods and sensors which can be employed so long as the air temperature remains lower than 100 degrees Celsius, and if there are semiconductor sensors which can be used at higher temperatures, they are not adapted for ambient conditions of the kind that is met with in hot air drying installations, which are close to saturation (4–10 Kg of water vapour per Kg of dry air at 120–140 degrees Celsius), and which may well be loaded with dust.

The invention aims to enable humidity of such hot air to be measured under satisfactory conditions.

To this end, in a first aspect, the invention proposes a method of measuring the humidity of hot air, characterised in that the said hot air is diluted under known conditions with cool air of known humidity in order to obtain an air mixture of reduced temperature, the humidity of the said air mixture is measured, and the humidity of the hot air is deduced from the known dilution conditions, from the known humidity of the cool air, and from the measured humidity of the air mixture.

By the selection of dilution conditions such that the temperature of the air mixture is low enough to enable its humidity to be measured by means of a conventional method having high precision and correct response time, the invention makes it finally possible to perform satisfactorily the deduction of the humidity of the hot air.

According to preferred features, in order to obtain the said air mixture, use is made of a suction source, a measuring chamber which is open only to the suction source and to a mixing chamber, and the said mixing chamber itself, which is open only to the measuring chamber, to the hot air and to the cool air, with dilution being carried out in a continuous mode in the mixing chamber while a regular stream of air mixture which comes from the mixing chamber and is directed towards the suction source, is passed through the measuring chamber.

The air mixture is thus automatically obtained in a simple and convenient way.

According to other preferred features, in order that the dilution conditions shall be known:

the aperture size or calibration of the orifices, through which the mixing chamber is open to the hot air and cool air respectively, is predetermined;

the pressure in the suction source is maintained at a predetermined constant value; and the pressure and temperature of the cool air and those of the hot air upstream of their respective calibrated orifices are measured or estimated.

this way, only simple operations have to be carried out over the course of time, since the pressure of the suction source can be held at a constant value automatically by virtue of the pressure regulator, while as to the above mentioned temperature and pressure measurements, these pose no particular problems.

According to further preferred features, in order to avoid condensation effects, the said hot air is reheated upstream of the mixing chamber, and the walls of the mixing and measuring chambers are heated.

In this connection, it is important to contend with all condensation effects, since if the latter occur, a certain amount of water vapour will no longer form a part of the air content, and measurement of it will be errored.

The above mentioned features enable the various possible causes of condensation to be simply and effectively overcome, in particular the reduction in pressure and temperature of the hot air in its path to the mixing chamber, the fact that the mixing and measuring chambers have walls which may be colder than the air contained in these latter, and the fact that the temperature within these chambers may not be high enough for all of the water contained in the air to be able to be maintained in the vapour phase.

According to further preferred features, in order to measure the humidity of the air mixture, a psychrometer disposed in the said measuring chamber is employed.

In this connection, the invention is compatible with use of this apparatus under relatively sensitive conditions (see below), with selection of this apparatus leading to benefits from the excellent accuracy which it can offer.

In a second aspect, the invention proposes apparatus for measuring the humidity of hot air, suitable for use in the method described above, characterised in that it includes:

a mixer for diluting, under known conditions, the said hot air with cool air of known humidity, so as to obtain an air mixture of reduced temperature; and a sensor for measuring the humidity of the said air mixture, for connection to a computer which is adapted to deduce the humidity of the hot air from information signals supplied by the said sensor, from the known humidity of the cool air, and from the known dilution conditions.

According to preferred features:

the said mixer comprises an enclosure adapted to communicate with the hot air source, with the cool air source, and with a suction source; the said enclosure being divided into a mixing chamber and a measuring chamber; the said mixing chamber being in communication only with the hot air source, the cool air source and the measuring chamber, the said measuring chamber being in communication only with the mixing chamber and the suction source so that dilution takes place in a continuous manner in the mixing chamber, while a regular stream of air mixture which comes from the mixing chamber and which is directed towards the suction source is passed through the measuring chamber; the said sensor for measuring the humidity of the air mixture being disposed in the said measuring chamber;

the said mixer includes a first orifice of predetermined calibration between the said mixing chamber and the hot air source, and a second orifice of predetermined calibration between the mixing chamber and the cool air source;

the apparatus further includes:

sensors for measuring the pressure and temperature of the hot air upstream of the said first orifice of predetermined calibration; and sensors for measuring the humidity, temperature and pressure of the cool air upstream of the said second orifice of predetermined calibration;

the pressure of the suction source being arranged to remain constant;

the said mixer includes means for reheating the said hot air between the hot air source and the upstream of the said first orifice of predetermined calibration;

the said mixer includes means for heating the walls of the mixing and measuring chambers.

In accordance with further preferred features, the said sensor for measuring the humidity of the air mixture is a psychrometer, and the said mixer includes in the said measuring chamber a duct having a predetermined cross section in which the psychrometer is disposed, the said duct being in communication with the said mixing chamber through a third orifice of predetermined calibration.

The fact that the air is obliged to pass through this orifice, which has a cross section much smaller than that of the mixing chamber, improves the quality of the mixture of hot and cool air.

The said orifice and the said duct also enable the flow velocity of the air in which the psychrometer is placed to be set, with the duct also protecting the psychrometer from the radiation emitted by the walls of the enclosure if they are hotter than the air mixture to which the psychrometer is exposed.

According to other preferred features, the psychrometer comprises a water supply tube which has in the measuring chamber a length which is adapted to bring to the temperature of the measuring chamber the water that is deposited on the wet temperature probe.

The water with which the wet temperature probe is moistened is thus heated in a particularly simple and reliable way.

In accordance with further preferred features, the said mixer includes a filter between the mixing chamber and the measuring chamber.

This prevents the humidity sensor from becoming dirty, and especially, if it consists of a psychrometer, it prevents the coat of the wet temperature probe, arranged to be soaked with water, from becoming dirty.

In a third aspect, the invention provides a hot air drying installation, characterised in that it includes an apparatus of the kind described above for measuring the humidity of the hot drying air.

Such an installation, in which the humidity of the hot drying air is thus established with high accuracy, offers the advantage that it enables fine control to be obtained in the characteristics of the latter, having regard to the state of the load which is being dried.

According to preferred features, the installation includes means such that the said apparatus can measure the humidity of the hot drying air respectively upstream and downstream of the load which is to be dried.

By comparing the upstream and downstream measurements, it is possible to establish with high precision what is the humidity given up by the load to the drying air, and thus to establish the state of the load itself.

In accordance with further preferred features, which offer the advantage that the drying installation can be automated to a greater or lesser extent:

the installation includes an automatic control unit which controls at least one of its component parts in response to information signals about humidity, given by the said apparatus for measuring the humidity of the hot drying air; and the said automatic control unit controls, in response to the information signals supplied by the humidity measuring apparatus, at least one of the following:

humidifying means for the drying air;
means for introducing fresh air;
drying air extraction means;
air circulating means; and
heating means.

The disclosure of the invention will now be continued with the description of an embodiment which is given below by way of non-limiting example, with reference to the attached drawings. In the latter:

FIG. 3 is a more detailed diagrammatic view, in elevation and cross section, of the apparatus for measuring the humidity of the hot air;

FIG. 4 is an enlargement of the central part of that apparatus;

Figure 1:
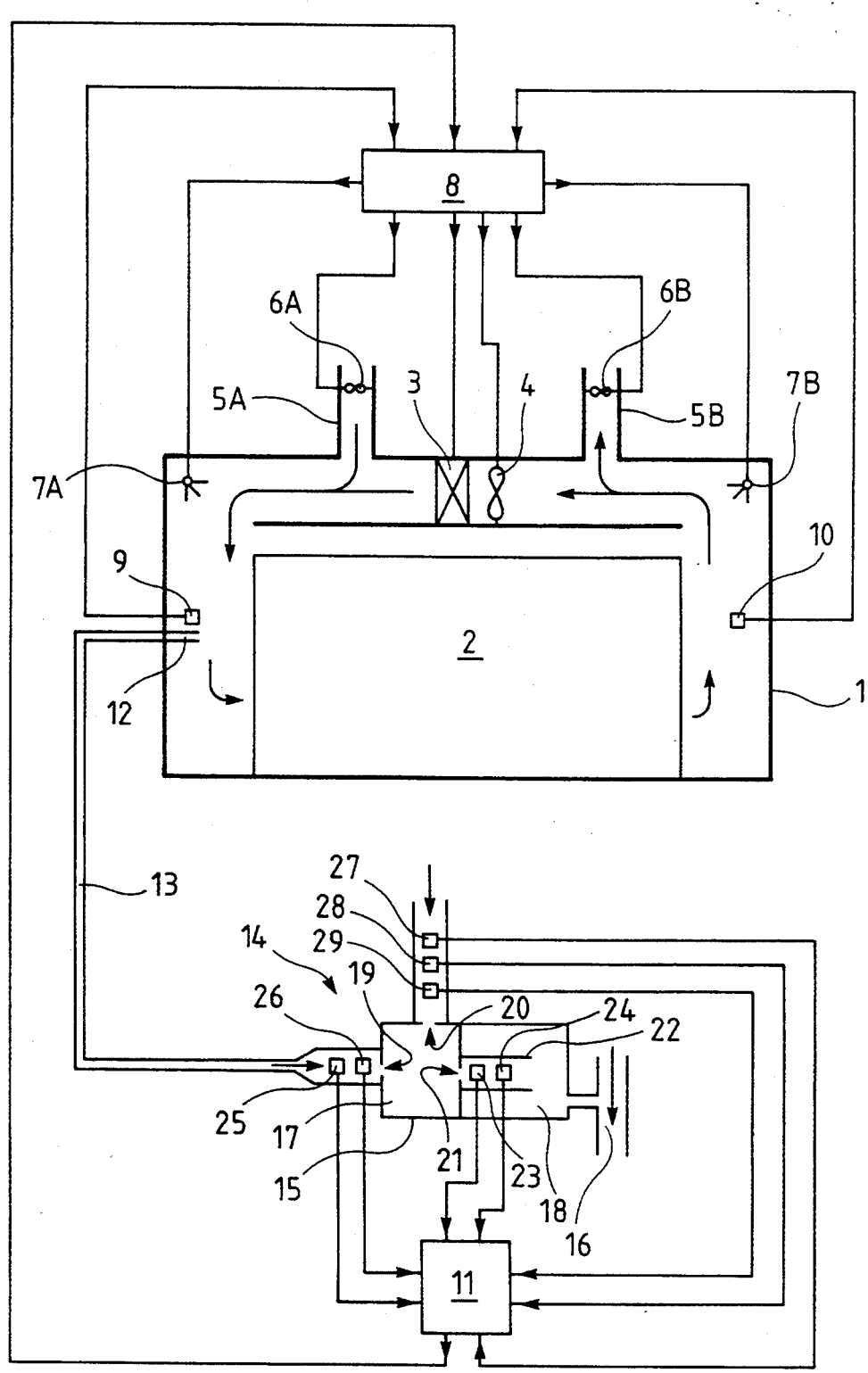
FIG. 1 shows diagrammatically a hot air drying installation in accordance with the invention.

The drying installation shown in FIG. 1 includes an oven 1, in which a load 2 of the product to be dried, which in this case is a mass of timber, is disposed. The oven 1 has a burner or a heating battery 3, a fan 4 for circulating air in the oven, two tubular mouthpieces 5A and 5B for extraction or introduction of air, in each of which a flap valve or fan 6A or 6B, respectively, is provided, and air humidifying devices 7A or 7B.

In order to cause the air to flow in the oven 1 as indicated by the arrows, the fan 4 rotates in the direction in which the air which it expels passes through the burner or heating battery 3, fresh air is introduced via the mouthpiece 5A and the flap valve or fan 6A, humidity is if necessary added to the air by the device 7A, the hot and possibly humidified air then comes into contact with the load 2, which it passes round and/or through before being drawn out by the fan 4, with the mouthpiece 5B serving for the extraction of part of the hot air, in a proportion which is set by the flap valve or fan 6B.

The oven 1 is arranged so that the direction of flow of the air can be reversed, with the fan 4 then drawing air from the burner or heating battery 3, the mouthpiece 5B being used for the introduction of fresh air, the device 7B for its humidification, and the mouthpiece 5A for extraction of the air.

The installation shown in FIG. 1 includes, for its control, an automatic control unit 8 which is connected to the burner or heating battery 3, to the fan 4, to the flap valves or fans 6A or 6B, and to the humidifiers 7A and 7B, so as to control the operation of these elements.

The automatic control unit 8 is also connected, for the purpose of receiving information signals in response to which it then controls the above mentioned elements, to temperature sensors 9 and 10 which are arranged on either side of the load 2 (i.e. upstream and downstream of the latter), and to a computer 11 which feeds it with a signal representing the humidity of air drawn from the oven 1 via the take-off port 12, which lies upstream of the load 2 when the drying air is flowing as shown.

The air take-off port 12 communicates with an insulated duct 13, which itself communicates with a mixer 14 which is arranged to dilute the hot drying air, under known conditions, with the cool air which in this example is air from outside and which is of known humidity, so as to obtain an air mixture the characteristics of which are compatible with the conditions of use of a conventional sensor adapted for measurement of the humidity of this air mixture. The temperature of the latter is for example of the order of 80 degrees Celsius.

The mixer 14 has an enclosure 15 which communicates with a suction source 16, besides the source of hot air constituted by the oven 1 and the source of cool air which is the outside air. This enclosure 15 is divided into a mixing chamber 17 and a measuring chamber 18, with the chamber 17 being in communication only with the hot air source, with the cool air source, and with the measuring chamber 18, the latter being in communication only with the mixing chamber 17 and suction source 16.

The suction source extracts air from the chamber 18, which in turn draws air from the mixing chamber 17, which itself draws air from the oven 1 and from outside. Continuous mixing thus occurs, in the chamber 17, between the air from the oven 1 and the air from outside, and a regular flow of air mixture coming from the chamber 17 and aspirated by the suction source 16 passes through the chamber 18.

The three orifices 19, 20 and 21 of the chamber 17, through which the latter communicates, respectively, with the hot air source (i.e. the oven 1), the source of cool air (i.e. air from outside) and the measuring chamber 18, all have predetermined calibrations, i.e. aperture sizes; and a duct 22 of predetermined cross section, which communicates with the chamber 17 through the orifice 21, is arranged in the chamber 18.

The calibration of the orifices 19 and 20 enables the conditions of dilution of the hot air by the cool air to be set, while the calibration of the orifice 21 and the cross section of the duct 22 enable the flow velocity of the air mixture in this duct to be set.

A sensor is disposed in this latter for measuring the humidity of the air mixture, and in this example it is a psychrometer comprising a pair of temperature probes, namely a dry temperature probe 23 and a wet temperature probe 24 having a cover which is soaked with water brought to the temperature of the air mixture.

For proper operation of the psychrometer, the calibration of the orifice 21 and the cross section of the duct 22 are so chosen that the air mixture has a velocity of the order of 2 m/s at the probes 23 and 24, with flow in normal operating mode.

In order to find out the state of dilution of the hot air by the cool air, it is necessary not only to know the calibrations of the orifices 19 and 20, but also to know temperature and pressure data, so that a temperature sensor 25 and a pressure sensor 26 have been provided just upstream of the orifice 19, while upstream of the orifice 20 there have been provided a pressure sensor 27 and a psychrometer having a dry temperature probe 28 and a wet temperature probe 29.

Each of the sensors and probes 23 to 29 is connected to the computer 11, which is arranged to deduce the humidity of the hot air from the information which they supply, and to deliver to the automatic control unit 8 a signal which corresponds to the calculated humidity.

In this connection, it is possible to obtain the humidity of the hot air from the humidity of the air mixture, from the humidity of the cool air, and from the dilution conditions, using the following formula:

$$X_{ip} = \frac{AX_i(\delta + X_{id}) + \delta(X_i - X_{id})}{A(\delta + X_{id}) - (X_i - X_{id})}$$

in which $X_{ip}$ is the absolute humidity of the hot air, $X_i$ is the absolute humidity of the air mixture, $X_{id}$ is the absolute humidity of the cool air, A is a factor representing the dilution conditions, and $\delta$ is a constant equal to 0.62198, which represents the ratio of the molar mass of the water vapour to that of the dry air.

$x_i$ and $x_{id}$ are deduced from the information signals supplied by the probes 23, 24 and 28, 29 respectively, in accordance with the psychrometric method.

The factor A, representing the dilution conditions, is obtained from the following formula:

$$A = K \frac{P_2 - P_3}{P_{ATM} - P_3} \frac{T_{ATM}}{T_2} \frac{P_2}{P_{ATM}}$$

where K is a constant which depends on the calibrations of the orifices 19 and 20, and which is established by experiment, $P_2$ is the pressure of the hot air measured by the sensor 26, $P_3$ is the pressure in the chamber 17, which is constant and which is established by experiment (the pressure of the suction source 16 is maintained constant for this purpose by means of a pressure regulator), $P_{ATM}$ is the pressure of the cool air detected by the sensor 27, $T_{ATM}$ is the temperature of the cool air detected by the dry temperature probe 28, and $T_2$ is the temperature of the hot air detected by the sensor 25.

It will be noted that it is possible in practice to consider that the pressure of the suction source remains constant as long as it lies in a certain relatively wide range, so that it is possible to make direct use of a conventional compressed air source in spite of the coarse character of its pressure regulation.

Figure 2:
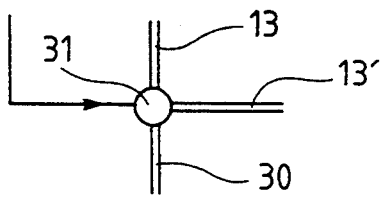
FIG. 2 shows a part of a variant of this installation in which a second hot air drying take-off is provided.

In the modification shown in FIG. 2, it is no longer the duct 13 that is connected directly into the mixer 14, but a duct 30, which is connected to the duct and to the duct 13' through a three-way valve 31 that puts the duct 30 into communication with either the duct 13 or the duct 13', with this latter being in communication with an air take-off arranged in the oven 1 on that side of the load 2 which is opposite to the take-off 12, the valve 31 being connected to the automatic control unit 8 that controls it. When the drying air flows as indicated by the arrows, and when the valve 31 puts the ducts 30 and 13 into communication with each other, the dry air with which the mixer 14 is in communication is then the drying air from upstream of the load 2, while it is the drying air from downstream when the valve 31 puts the duct 30 into communication with the duct 13'.

It will be noted that the apparatus comprising the mixer 14 and the sensors and probes connected to the computer 11 have a response time which is relatively rapid, and which is in any case considerably faster than the above mentioned semiconductor sensors, the response time of which is about 10 mn. Under certain conditions it is therefore possible to assume that the humidity of the upstream and downstream drying air has not varied during the time that the upstream humidity and downstream humidity, respectively, were being computed, and it is finally possible to assume that the difference between the two computed humidity values corresponds to the humidity released to the drying air by the load 2.

Figure 5:
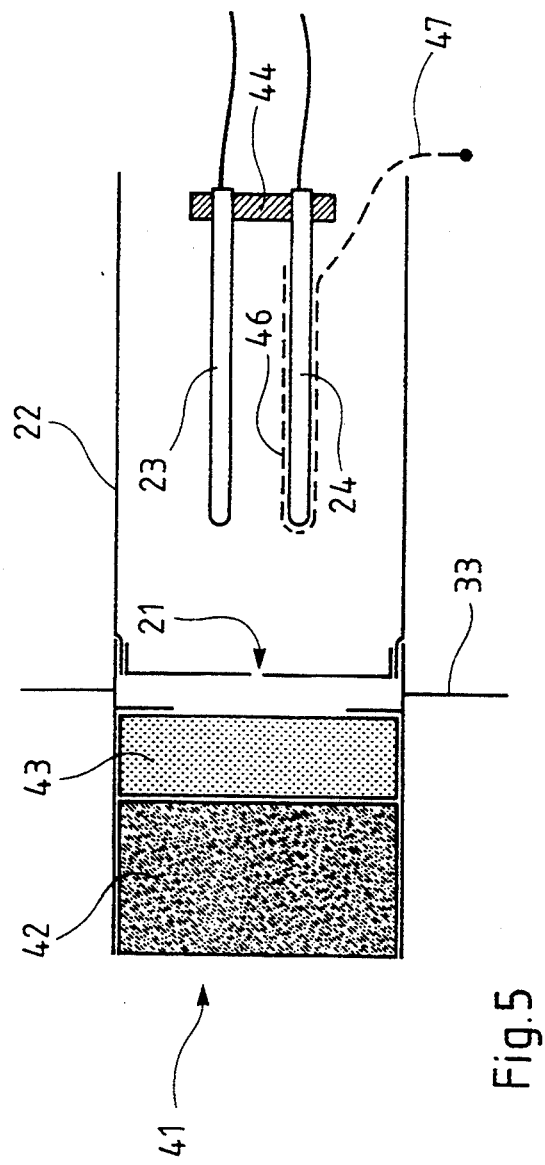
FIG. 5 is a top plan view of this portion in cross section.

The apparatus for measuring the humidity of the hot air is shown in greater detail in FIGS. 3 to 5, in which the sensors and probes 25 to 29 are however not shown.

The enclosure 15 has a generally cylindrical shape, the outer side wall 32 of which is common to the chambers 17 and 18, with the latter being separated from each other by a transverse annular wall 33, with each of the chambers 17 and 18 being closed on the opposite side from the wall 33 by a transverse wall 34 or 35 respectively.

Electrical heater rings 36, fed via the cable 37, are provided on the outer side of the wall 32, and since the latter, like the walls 33 and 34 in contact with the outside, is of metal, the heat communicated by the rings 36 is transmitted into all these walls. In order to avoid heat losses, the mixer 14 includes a layer 38 of thermal insulation around the wall 32. It is also possible to provide one on the outer side of the walls 34 and 35.

The walls of the chambers 17 and 18 in contact with the outside are heated by the rings 36 to a temperature which is higher than that of the air contained in the said chambers, so as to avoid condensation effects both on their walls and within the actual interior of the chambers, with the heat generated enabling the air which is in the latter to reach a temperature such that all the water vapour that it contains remains in the vapour phase (i.e. a temperature such that the saturating vapour pressure is greater than that of the dew point). Several heating rings 36 are distributed along the walls 32 so that the temperature shall be as uniform as possible in the enclosure 15, with a view to prevent condensation due to changes in the air temperature.

The wall 33 and the tube 22 are normally at the same temperature as the air contained in the enclosure 15, because they are entirely submerged in this air. The tube 22 can also serve to protect the probes 23 and 24 from radiation emitted by the wall 32, which is hotter. In the event of this radiation giving rise to an increase in the temperature of the tube 22, it is possible to arrange within the latter an anti-radiation screen comprising a reflective surface in facing relationship to the inner wall of the tube.

Naturally, an increase in the temperature within the enclosure 15 above the maximum operating temperature of the psychrometer (i.e. the boiling point of water) is avoided.

A heating cartridge 39, fed via a cable 40, is disposed in a terminal enlargement of the duct 13, close to the orifice 19 but upstream of the sensors 25 and 26. The cartridge 39 is arranged to heat, substantially uniformly, the air passing through it with a view to preventing any condensation effects.

In this connection, when the hot air passes through the duct 13 to the chamber 17, it undergoes a certain reduction in pressure and temperature which would be liable to cause condensation if the air were not reheated beforehand, and the heating effect given by the cartridge 39 is also useful because of the losses of pressure and heat losses which occur between the air take-off 12 and the terminal portion of the duct 13.

A filter 41 is arranged between the chambers 17 and 18, and more precisely in the chamber 17 upstream of the orifice 21. The filter 41 includes a first plug 42 which, here, is of rock wool, together with a second plug 43 which in this example is of sintered bronze (see FIGS. 4 and 5). This filter serves to protect the psychrometer from any dust in the air mixture.

The probes 23 and 24 are disposed in the duct 22 side by side and at the same level, by means of a support 44, with the wet temperature probe 24 being overhung by the end of a tube 45 for supplying moistening water for the coat 46, in the shape of a finger of a glove, with which the probe 24 is covered. A braid 47 attached to the coat 46 is provided for the purpose of removing any excess water from the duct 22, so that such excess remains moderate.

The tube 45 is of a thermally conducting material, being of copper in this example, and it includes in the chamber 18 a certain number of coils 48, only three of which are shown in FIG. 3, so that within that chamber its length will be great enough for the moistening water to remain within it long enough for the drops deposited on the coat 46 to be at the same temperature as the chamber 18. In this way the need to control and regulate the temperature of the moistening water is avoided.

In the example shown, the flow rate of the moistening water (a few drops per minute) has been determined by experiment, but in a modification it is possible to regulate this flow by monitoring the signals given by the wet temperature probe in order to detect any sudden variation that signifies that the Goat 46 is drying out, and a control means for the flow in the tube 45 can consequently be operated so as to wet the coat 46 again.

The suction source 16 comprises an ejection tube 49 which is supplied with compressed air through the tube 50, in such a way that the air is drawn in via the tube 51 that connects the tube 49 to the chamber 18. It will be seen that the tube 51 exhausts in the lowest part of the chamber 18, so that any excess of water that has been deposited in it by the braid 47 will also be drawn up.

As described above, the pressure of the compressed air in the tube 50 is maintained constant by means of a pressure regulator not shown, which in this example directly regulates the pressure of the compressed air source.

In general terms, the value of this pressure, and the dimensioning of the mixer 14 (i.e. the volume of the chambers 17 and 18, the calibrations of the orifices 19 to 21, and the cross section of the duct 22) are so chosen as to give good mixing in the chamber 17, and to give the air mixture in the duct 22 a flow velocity which is suitable for the use of a psychrometer, that is to say a velocity of the order of 2 m/s.

The overall flow rate within the enclosure 15 is thus relatively small in relation to the cross section of the chambers 17 and 18, and it will also be noted in this regard that it is important to have a low flow rate in order to maximise the useful life of the filter 41.

Under these conditions it can be assumed that the pressure in the chamber 17 remains constant and homogeneous, so that there is no need to provide a permanent sensor for measuring it.

Figure 6:
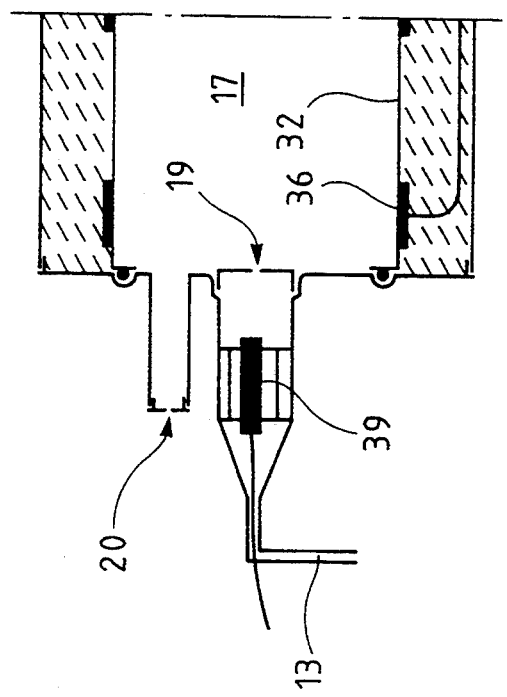
FIG. 6 is a partial view similar to FIG. 3, showing a variant in the arrangement of the fresh air take-off.

The locations of the orifices 19, 20 and 21, which are arranged at the centre of the wall 34, in the wall 32 and at the centre of the wall 33 respectively, has also been chosen in accordance with the above mentioned requirements, although other locations may be suitable, and especially that shown in FIG. 6 in which the orifice 20 is arranged at the end of a tube which is open in the wall 34.

In a modification which is not shown, the computer 11 is omitted, its function then being directly assumed by the automatic control unit 8, with the latter also serving to regulate the flow of moistening water in the tube 25 in accordance with the above mentioned method in which the signal from the temperature probe 24 is monitored, and with the control unit 8 also controlling the heater rings 36 and the cartridge 39 in response to the temperature in the enclosure 15 given by the dry temperature probe 23.

In another modification not shown, which may be employed when circumstances permit, the temperature, pressure and humidity of the cool air, and even the temperature and pressure of the hot air, are simply estimated rather than being measured with the sensors and probes 25 to 29.

Finally it will be noted that, according to the degree of precision required, it is possible to replace the psychrometers with humidity sensors of another type; that the apparatus described can be employed to measure the humidity of any kind of air other than that in a drying oven; and that in the event of a major variation in temperature in the air to be measured, it is possible to close off the cool air orifice for periods of time in which the characteristics of the hot air enable its humidity to be measured directly by the sensor which is arranged in the measuring chamber.

The invention is of course not limited to the examples described and shown.

I claim:

1. A method of measuring a humidity of hot air, comprising the steps of:
   diluting the hot air under known conditions with cool air of known humidity in order to obtain an air mixture of reduced temperature;
   measuring the humidity of the air mixture; and
   calculating the humidity of the hot air based on the known dilution conditions, the known humidity of the cool air, and the measured humidity of the air mixture.

2. A method according to claim 1, wherein the air mixture is created using a suction source which draws the air mixture from a mixing chamber into a measuring chamber which is open only to the suction source and to the mixing chamber, wherein the mixing chamber is open only to the measuring chamber a source of hot air and a source of cool air, with dilution being carried out in a continuous mode in the mixing chamber while a stream of air mixture, which is directed from the mixing chamber toward the suction source, is passed through the measuring chamber.

3. A method according to claim 2, further comprising the steps of:
   calibrating a dimensions of a first orifice, through which the mixing chamber is open to the source of hot air;
   calibrating a dimensions of a second orifice, through which the mixing chamber is open to the source of cool air;
   maintaining a pressure applied by the suction source at a predetermined constant value; and
   determining a pressure and temperature of the cool air and a pressure and temperature of the hot air, upstream of the first orifice and the second orifice, respectively.

4. A method according to claim 2, wherein, in order to avoid condensation effects, the hot air is reheated upstream of the mixing chamber, and walls of the mixing and measuring chambers are heated.

5. A method according to claim 2, wherein a psychrometer is disposed in the measuring chamber to measure the humidity of the air mixture.

6. An apparatus for measuring a humidity of hot air in fluid communication with a source of hot air and in fluid communication with a source of cool air of known humidity, comprising:
   a mixer for diluting, under known conditions, hot air from the source of hot air with cool air from the source of cool air, so as to obtain an air mixture of reduced temperature;
   a first humidity sensor for measuring the humidity of the air mixture; and
   a computer coupled to the first humidity sensor for calculating the humidity of the hot air based on the humidity of the air mixture detected by the first humidity sensor, the known humidity of the cool air and the known dilution conditions.

7. An apparatus according to claim 6, further comprising a suction source, wherein the mixer comprises an enclosure adapted to communicate with the source of hot air, with the source of cool air and with the suction source, wherein the enclosure is divided into a mixing chamber and a measuring chamber, the mixing chamber being in fluid communication only with the source of hot air, the source of cool air and the measuring chamber and wherein the measuring chamber is in fluid communication only with the mixing chamber and the suction source so that the dilution takes place in a continuous manner in the mixing chamber, while a regular stream of air mixture which comes from the mixing chamber and which is directed towards the suction source is passed through the measuring chamber, and wherein the first humidity sensor for measuring the humidity of the air mixture is disposed in the measuring chamber.

8. An apparatus according to claim 7, wherein the mixer includes a first orifice of predetermined calibration between the mixing chamber and the source of hot air, and a second orifice of predetermined calibration between the mixing chamber and the source of cool air.

9. Apparatus according to claim 8, further comprising:
   a first pressure sensor for measuring the pressure of the hot air upstream of the first orifice;
   a first temperature sensor for measuring the temperature of the hot air upstream of the first orifice;
   a second humidity sensor for measuring the humidity of the cool air upstream of the second orifice;
   a second pressure sensor for measuring the pressure of the cool air upstream of the second orifice; and
   a second temperature sensor for measuring the temperature of the cool air upstream of the second orifice;
   wherein the pressure applied by the suction source is constant.

10. An apparatus according to claim 8, wherein the mixer includes means for reheating the hot air upstream of the first orifice.

11. An apparatus according to claim 6, wherein the mixer includes means for heating walls of a mixing chamber and a measuring chamber.

12. An apparatus according to claim 7, wherein the first humidity sensor is a psychrometer, and wherein the mixer includes, in the measuring chamber, a duct in fluid communication with the mixing chamber through a third orifice of predetermined calibration.

13. An apparatus according to claim 12, wherein the psychrometer comprises a water supply tube which extends into the measuring chamber a length which is predetermined to bring a temperature of water on a wet temperature probe to a temperature of the measuring chamber.

14. An apparatus according to claim 7, wherein the mixer includes a filter between the mixing chamber and the measuring chamber.

15. An apparatus according to claim 6, wherein the apparatus is included in a hot air drying installation, wherein the apparatus is employed for measuring the humidity of the hot drying air.

16. An apparatus according to claim 15, including means for measuring the humidity of the hot drying air upstream and downstream of a load which is to be dried.

17. An apparatus according to claim 15, further including an automatic control unit which controls at least one of components of the installation in response to the humidity measured by the apparatus.

18. An apparatus according to claim 17, wherein the automatic control unit controls, in response to the humidity measured by the humidity measuring apparatus, at least one of the following:
- humidifying means for humidifying the drying air;
- means for introducing fresh air into the drying air;
- drying air extraction means for extracting the drying air from the measuring chamber; and
- heating means for heating the drying air.

* * * * *

UNITED STATES PATENT AND TRADEMARK OFFICE
CERTIFICATE OF CORRECTION

PATENT NO. : 5,431,040  
DATED : 11 July 1995  
INVENTOR(S) : Bruno AIME It is certified that error appears in the above-identified patent and that said Letters Patent is hereby corrected as shown below:

| Column | Line | | |
|---|---|---|---|
| 1 | Before 10 | Insert: | --BACKGROUND OF THE INVENTION--. |
| 1 | Before 21 | Insert: | --SUMMARY OF THE INVENTION--. |
| 1 | 63 | Before "this" insert --In--. | |
| 2 | 17 | Delete "able to be". | |
| 3 | 56 | Delete "what is". | |
| 4 | Before 6 | Insert: | --BRIEF DESCRIPTION OF THE DRAWINGS--. |
| 4 | Before 23 | Insert: | --DETAILED DESCRIPTION--. |
| 8 | 18 | Change "Goat" to --coat--. | |
| 9 | 36 | After "chamber" insert --,--. | |

UNITED STATES PATENT AND TRADEMARK OFFICE
CERTIFICATE OF CORRECTION

PATENT NO. : 5,431,040

DATED : 11 July 1995

INVENTOR(S) : Bruno AIME

It is certified that error appears in the above-identified patent and that said Letters Patent is hereby corrected as shown below:

| Column | Line | |
|---|---|---|
| 9 | 44 | After "calibrating" delete "a". |
| 9 | 47 | After "calibrating" delete "a". |
| 10 | 34 | Change "Apparatus" to --An apparatus--. |

Signed and Sealed this

Twelfth Day of December, 1995

Attest:

BRUCE LEHMAN

Attesting Officer

Commissioner of Patents and Trademarks